(12) United States Patent
Farnham

(10) Patent No.: US 8,304,572 B2
(45) Date of Patent: Nov. 6, 2012

(54) SYNTHESIS OF FLUOROALCOHOL-SUBSTITUTED (METH)ACRYLATE ESTERS AND POLYMERS DERIVED THEREFROM

(75) Inventor: William Brown Farnham, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/104,997

(22) Filed: May 11, 2011

(65) Prior Publication Data

US 2011/0213175 A1    Sep. 1, 2011

Related U.S. Application Data

(62) Division of application No. 12/061,707, filed on Apr. 3, 2008, now abandoned.

(60) Provisional application No. 60/909,950, filed on Apr. 4, 2007.

(51) Int. Cl.
C07C 69/73    (2006.01)
(52) U.S. Cl. ...................................................... 560/183
(58) Field of Classification Search .................... None
See application file for complete search history.

(56) References Cited

U.S. PATENT DOCUMENTS 6,653,419 B1    11/2003    Petrov et al.
6,784,312 B2    8/2004    Miyazawa et al.

OTHER PUBLICATIONS

V. Petrov, Synthesis of Polyfluorinated Tertiary Alcohols Using Ring Opening Reactions of 2,2-Bis(trifluoromethyl) Oxirane, Synthesis, 2002, pp. 2225.

*Primary Examiner* — Yevegeny Valenrod

(57) ABSTRACT

This invention relates to processes for preparing fluoroalcohol-substituted (meth)acrylate esters. This invention also relates to block copolymers incorporating repeat units derived from fluoroalcohol-substituted (meth)acrylate esters, and photoresists derived therefrom.

4 Claims, No Drawings

SYNTHESIS OF FLUOROALCOHOL-SUBSTITUTED (METH)ACRYLATE ESTERS AND POLYMERS DERIVED THEREFROM

FIELD OF THE INVENTION

This invention relates to processes for preparing fluoroalcohol-substituted (meth)acrylate esters. This invention also relates to block copolymers incorporating repeat units derived from fluoroalcohol-substituted (meth)acrylate esters, and photoresists derived therefrom.

BACKGROUND

Miyazawa et al. (U.S. Pat. No. 6,784,312) discloses polymerizable monomers represented by the general formula $$CH_2=C(R^1)CO_2-R^2-[C(CF_3)_2OR^3]_n,$$

wherein $R^1$ is a hydrogen atom, a halogen atom, a hydrocarbon group or a fluorine-containing alkyl group; $R^2$ is a straight-chain or branched alkyl group, a cyclic alkyl group, an aromatic group, or a substituent having at least two of these groups, the $R^2$ being optionally partially fluorinated; $R^3$ is a hydrogen atom, a hydrocarbon group that is optionally branched, a fluorine-containing alkyl group, or a cyclic group having an aromatic or alicyclic structure, the $R^3$ optionally containing a bond of an oxygen atom or carbonyl group; and n is an integer of 1-2. Methods for synthesizing such monomers are also disclosed.

HFIBO (hexafluorobutylene oxide) is known to undergo ring-opening reactions with a variety of species to give fluoroalcohol-substituted products which range from 1/1 adducts to substituted HFIBO oligomers. (V. Petrov, Synthesis 2002, 2225; see also U.S. Pat. No. 6,653,419).

Nevertheless, there remains a need for a commercially viable synthetic route to certain fluoroalcohol-substituted (meth)acrylates that can be used to prepare fluoroalcohol-substituted polymers.

SUMMARY OF THE INVENTION

One aspect of this invention is a process for the preparation of $CH_2=C(R)CO_2CH_2C(R_f)_2OH$, comprising reacting $CH_2=C(R)CO_2H$ with a fluorinated epoxide, 3,

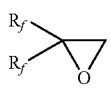

in the presence of a catalyst, wherein R is H or a $C_1$-$C_4$ alkyl group, and $R_f$ is a fluorinated $C_1$-$C_{10}$ alkyl group.

Another aspect of this invention is a block copolymer comprising repeat units derived from $CH_2=C(R)CO_2CH_2C(R_f)_2OH$.

Another aspect of this invention is a photoresist comprising a photoactive component and a block copolymer derived from $CH_2=C(R)CO_2CH_2C(R_f)_2OH$.

DETAILED DESCRIPTION

One aspect of this invention is a process for preparing a (meth)acrylate ester of formula $CH_2=C(R)CO_2CH_2C(R_f)_2OH$, comprising reacting $CH_2=C(R)CO_2H$ with a fluorinated epoxide 3,

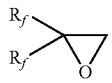

in the presence of a catalyst, wherein R is H or a $C_1$-$C_4$ alkyl group, and $R_f$ is a fluorinated $C_1$-$C_{10}$ alkyl group. The term "(meth)acrylate ester" denotes an acrylate ester when R=H, and a methacrylate ester when R=$CH_3$.

Suitable catalysts for the preparation of $CH_2=C(R)CO_2CH_2C(R_f)_2OH$ include PPN chloride and quaternary ammonium halides. Typical catalyst loadings are from 0.2 to 1.0 mol %.

In one embodiment, R is selected from H and methyl, and $R_f$ is $CF_3$.

The reaction conditions are mild: the reaction temperature is typically 30° C. to 90° C. and the reaction pressure is typically 1.0 to 5.0 atm. Higher pressures can also be used to shorten batch time, but possibly at the expense of more difficult temperature control. In one embodiment, HFIBO is initially added to the (meth)acrylic acid and catalyst at room temperature, and then the reaction temperature is increased to maintain reflux conditions. Use of a solvent is optional.

The desired product, $CH_2=C(R)CO_2CH_2C(R_f)_2OH$, can be used in some applications without further purification, or can be purified by standard methods such as distillation.

The fluoroalcohol-substituted esters, $CH_2=CHCO_2CH_2C(CF_3)_2OH$ 1 and $CH_2=C(CH_3)CO_2CH_2C(CF_3)_2OH$ 2, are formed in nearly quantitative yield from acrylic acid and methacrylic acid, respectively:

$$CH_2=CHCO_2H + HFIBO \rightarrow CH_2=CHCO_2CH_2C(CF_3)_2OH \qquad 1$$

$$CH_2=C(CH_3)CO_2H + HFIBO \rightarrow CH_2=C(CH_3)CO_2CH_2C(CF_3)_2OH \qquad 2$$

The fluorinated epoxides, 3, can be prepared by reacting fluorinated ethylenically unsaturated compounds with metal hypohalite oxidizing agents in the presence of phase transfer catalysts, as described in U.S. Pat. No. 6,653,419 which is incorporated herein by reference.

The fluoroalcohol-substituted esters can be used to prepare polymers comprising a repeat unit derived from $CH_2=C(R)CO_2CH_2C(R_f)_2OH$, wherein R is H or a $C_1$-$C_4$ alkyl group, and $R_f$ is a fluorinated $C_1$-$C_{10}$ alkyl group. The polymer can be a homopolymer, a block copolymer, a random copolymer, or a gradient copolymer, wherein a copolymer further comprises repeat units derived from substituted or unsubstituted (meth)acrylic acids or esters, substituted or unsubstituted styrenes, vinyl acetate, or acrylonitrile. The polymers and copolymers can be capped or uncapped.

One aspect of this invention is a block copolymer of the form $A_m$-$B_n$, wherein m and n are integers greater than 2; each A is independently selected and each A is a repeat unit derived from an acrylic monomer selected from the group consisting of $CH_2=C(R)CO_2CH_2C(R_f)_2OH$ and $CH_2=CR^1CO_2R^2$, wherein R is H or a $C_1$-$C_4$ alkyl group; $R_f$ is a fluorinated $C_1$-$C_{10}$ alkyl group; $R^1$ is selected from the group consisting of H, F, $C_1$-$C_5$ alkyl, and $C_1$-$C_5$ fluoroalkyl; $R^2$ is selected from the group consisting of $C_1$-$C_{20}$ acyclic alkyl, $C_5$-$C_{50}$ cyclic alkyl, and $C_7$-$C_{50}$ polycyclic alkyl; and each B is independently selected and is a repeat unit derived from styrene or an acrylic monomer selected from the group consisting of $CH_2=C(R)CO_2CH_2C(R_f)_2OH$ and $CH_2=CR^3CO_2R^4$, wherein $R^3$ is selected from the group consisting of H, F, $C_1$-$C_5$ alkyl, and $C_1$-$C_5$ fluoroalkyl; and $R^4$ is selected from the group consisting of —C(R$^5$)(R$^6$)(CH$_2$)$_p$ R$_f$, —C(R$^5$)((CH$_2$)$_p$R$^7$)$_2$, —(CH$_2$)$_p$R$^7$, and —(CH$_2$)$_p$O (CH$_2$)$_p$ R$^7$, wherein p is an integer from 1 to 4; R$^7$ is C$_2$-C$_{14}$ perfluoroalkyl; and R$^5$ and R$^6$ are independently selected from the group consisting of H, C$_1$-C$_3$ alkyl, or taken together form a 5- or 6-membered ring.

In the block copolymer, either the A block, the B block, or both the A and B blocks, can contain a repeat unit derived from a fluoroalcohol-substituted (meth)acrylate ester of formula CH$_2$=C(R)CO$_2$CH$_2$C(R$_f$)$_2$OH.

Polymers of fluoroalcohol-substituted (meth)acrylate esters can be prepared by any method suitable for polymerizing or copolymerizing (meth)acrylic esters. For example, homopolymers can be prepared by conventional radical initiators, as illustrated in Example 6. Alternatively, RAFT (reversible addition fragmentation chain transfer) polymerizations can be used, as illustrated in Example 8. RAFT processes using xanthate or dithiocarbamate chain transfer RAFT agents are disclosed in WO 99/31144 which is incorporated by reference. RAFT processes using dithioester or trithiocarbonate chain transfer agents are disclosed in WO 98/01478, WO 200500319, WO 2005000924 and WO 2005000923. These references are herein incorporated in their entirety.

Block co-polymers of fluoroalcohol-substituted (meth) acrylate esters can be prepared by, for example, RAFT polymerization, in which first monomer A is polymerized and then monomer B is added to the reaction mixture when monomer A is substantially consumed. This process can be repeated to make alternating ABA, ABAB, ABABA, etc. block copolymers. Alternatively, each A block can comprise a random mixture of repeat units derived from a mixture of A monomers. Similarly, each B block can comprise a random mixture of repeat units derived from a mixture of B monomers.

One aspect of this invention is a photoresist comprising a photoactive component and a block copolymer of the form A$_m$-B$_n$, wherein the photoactive component (PAC) is a compound that affords either acid or base upon exposure to actinic radiation. If an acid is produced upon exposure to actinic radiation, the PAC is termed a photoacid generator (PAG). If a base is produced upon exposure to actinic radiation, the PAC is termed a photobase generator (PBG). Several suitable photoacid generators are disclosed in WO 00/66575 which is incorporated by reference.

Suitable photoacid generators include, but are not limited to, 1) sulfonium salts (structure I), 2) iodonium salts (structure II), and 3) hydroxamic acid esters, such as structure III.

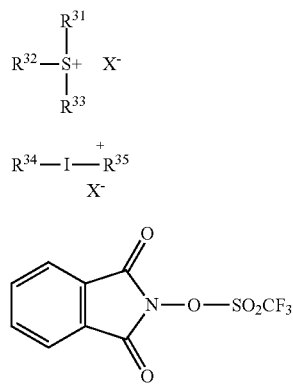

In structures I-II, R$^{31}$-R$^{35}$ are independently substituted or unsubstituted aryl or substituted or unsubstituted C$_7$-C$_{20}$ alkylaryl (aralkyl). Representative aryl groups include, but are not limited to, phenyl and naphthyl. Suitable substituents include, but are not limited to, hydroxyl (—OH) and C$_1$-C$_{20}$ alkyloxy (e.g., —OC$_{10}$H$_{21}$). The anion, X$^-$, in structures I-II can be, but is not limited to, SbF$_6^-$ (hexafluoroantimonate), CF$_3$SO$_3^-$ (trifluoromethylsulfonate=triflate), and C$_4$F$_9$SO$_3^-$ (perfluorobutylsulfonate).

EXAMPLES

The following examples illustrate certain features and advantages of the present invention. They are intended to be illustrative of the invention, but not limiting. All percentages are by weight, unless otherwise indicated.

Definition of Chemicals and Monomers Used (Commercial Source)

PPN chloride=Bis(triphenylphosphoranylidene)ammonium chloride

HFIBO=hexafluoroisobutene oxide methyl adamantyl methacrylate (Idemitsu Japan, Tokyo, Japan)

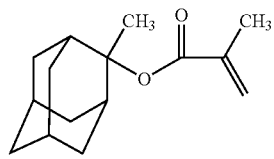

NBLMA=(Kuraray Co., Ltd., Tokyo, Japan)

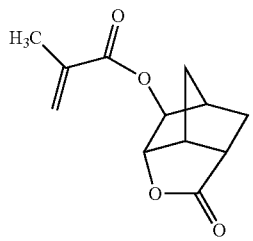

THF=Tetrahydrofuran (Sigma-Aldrich Chemical Co., Milwaukee, Wis.)

V-601=Dimethyl 2,2'-azobis(isobutryate)—(Wako Chemicals USA, Richmond, Va.)

V-501=4,4'-Azobis(4-cyanopentanoic acid)—(Wako Chemicals USA, Richmond, Va.)

Characterization Methods

Size exclusion chromatography with the triple detection method was carried out using an SEC system Model Alliance 2690™ from Waters Corporation (Milford, Mass.), with a Waters 410™ refractive index detector (DRI) and Viscotek Corporation (Houston, Tex.) Model T-60A™ dual detector module incorporating static right angle light scattering and differential capillary viscometer detectors. Data reduction, incorporating data from all three detectors (refractometer, viscometer and light scattering photometer (right angle)), was performed with Trisec® GPC version 3.0 by Viscotek. The Flory-Fox equation was used for angular asymmetry light scattering correction. All chromatographic columns were obtained from Polymer Laboratories (Church Stretton, UK): two PL Gel Mixed C linear columns and one PL Gel 500A column to improve resolution at low molecular weight region of a polymer distribution. The mobile phase was THF, stabilized with 0.05% BHT from J. T Baker, Phillipsburg, N.J.

Example 1

Preparation of $CH_2=C(CH_3)CO_2CH_2C(CF_3)_2OH$ from Methacrylic Acid and HFIBO A 3-neck flask fitted with thermocouple, septum, and reflux condenser (5° C.) was charged with methacrylic acid (8.61 g, 0.1 mol) and PPN chloride (0.57 g, 1.0 mmol). HFIBO (19.3 g, 0.107 mol) was added by means of a canula, starting at room temperature. The mixture was heated to reflux (ca. 48° C., liquid temperature). As the boil-up rate diminished, the bath temperature was increased so that reflux was re-established, but at higher residual liquid temperature. The reaction temperature was increased in stages to 85° C. and was maintained at this value for 0.5 hr.

$^1H$ NMR($C_6D_6$): 6.10 (s, a=10.48), 5.25 (s, a=10.50), 4.35 (apparent s, a=31.37; $CH_2$+OH), 1.75 (s, a=31.4), in accord with $CH_2=C(CH_3)CO_2CH_2C(CF_3)_2OH$. No signals for methacrylic acid were observed. $^{19}F$ NMR($C_6D_6$): −76.45 (s, a=96.5), −73.18 (s, a=3.4, starting epoxide).

Distillation afforded 24.7 g (93%) of colorless oil, b.p. 47-48° C./4 mm. $^1H$ NMR($C_6D_6$): 5.96 (s, a=1.00), 5.12 (s, a=1.00), 4.22 (bd s) and 4.20 (s, combined a=2.90), 1.63 (s, a=3.03), in accord with desired ester. $^{19}F$ NMR($C_6D_6$): −76.45 (s, a=100).

Example 2

Preparation of $CH_2=C(CH_3)CO_2CH_2C(CF_3)_2OH$ from Methacrylic Acid and HFIBO A 2 liter 3-neck flask fitted with thermocouple, septum, and reflux condenser (5° C.) was charged with methacrylic acid (344.4 g, 4.0 mol) and PPN chloride (7.41 g, 13 mmol, 0.33 mol %). HFIBO (770.4 g, 4.28 mol) was added by means of a canula, starting at room temperature. The septum was replaced and the mixture was heated to reflux (ca. 48° C., internal). As the boil-up rate diminished, the reaction temperature was increased so that reflux was re-established at higher residual liquid temperature. The bath temperature was increased over a 4 hr period so that the internal pot temperature eventually increased to 88° C. The mixture was maintained at ca. 84° C.-88° C. for 0.5 hr, and then allowed to cool.

The mixture was transferred to a 1 liter vessel and was distilled using a 20 cm Vigreux column, operating at ca. 4 mm. Some HFIBO was recovered in a cold trap (−78° C.; 20.8 g, 2.7% of initial charge), then a small forerun was collected (8.8 g). The major portion of product was collected in one fraction (ca. 42-44° C./4 mm), obtaining 1040 g (98.3%) of colorless liquid.

$^1H$ NMR($C_6D_6$): 6.10 (s, a=11.8), 5.30 (s, a=11.8), 4.5 (bd s) and 4.38 (s, combined a=35.3; $CH_2$+OH), 1.75 (s, a=34.8), in accord with desired ester. No other signals were detected. Purity estimate: >99.5%.

$^{19}F$ NMR($C_6D_6$): −76.5 (s, a=100).

Example 3

Preparation of $CH_2=CHCO_2CH_2C(CF_3)_2OH$ from Acrylic Acid and HFIBO

A 3-neck flask fitted with thermocouple, septum, and reflux condenser (5° C.) was charged with acrylic acid (7.2 g, 0.1 mol) and PPN chloride (0.57 g, 1.0 mmol). HFIBO (18.0 g, 0.1 mol) was added at room temperature by means of a canula. The mixture was heated to reflux (ca. 48° C., internal liquid). As the boil-up rate diminished, the reaction temperature was increased gradually over 2.5 hr to 85° C. The mixture was cooled and sampled for NMR.

$^1H$ NMR($C_6D_6$): 6.10 (d, 1H), 5.65 (dd, 1H), 5.20 (d, 1H), 5.0 (bd s, 1H), 4.25 (s, 2H).

$^{19}F$ NMR($C_6D_6$): major s at −76.47.

Spectra are in accord with nearly exclusive formation of the desired ester, $CH_2=CHCO_2CH_2C(CF_3)_2OH$, accompanied by a minor amount of unconverted acrylic acid. Product was distilled to give a colorless oil, b.p. ca. 32° C./1.8 mm, obtained in two fractions, 3.95 g and 17.86 g. NMR analysis of the larger fraction showed nearly pure ester (>97%).

Example 4

Preparation of $CH_2=CHCO_2CH_2C(CF_3)_2OH$ from Acrylic Acid and HFIBO

A 3-neck flask fitted with thermocouple, septum, and reflux condenser (5° C.) was charged with acrylic acid (72.0 g, 1.0 mol) and PPN chloride (2.85 g, 5.0 mmol). HFIBO (189 g, 1.05 mol) was added at room temperature by means of a canula. The mixture was heated to reflux and the bath temperature was increased gradually so that the internal liquid temperature rose to 85° C. and was maintained for 0.5 hr. NMR analysis revealed no detectable acrylic acid.

The reaction mixture was transferred to a 500 mL round bottom flask containing phenothiazine (0.5 g) and butoxyphenol (0.1 g) and product was distilled to provide ca. 1 mL of forerun, b.p. 25-55° C./8.9 mm and then a constant-boiling liquid, 55° C./8.9 mm, 214.3 g (yield estimate=85%).

$^1H$ NMR($C_6D_6$): 6.10 (d, 1H), 5.67 (dd, 1H), 5.19 (d, 1H), 4.27 (bd s, 1H), 4.18 (s, 2H). $^{19}F$ NMR($C_6D_6$): −76.48 (s). Purity estimate >99.5%.

Example 5

Preparation of $CH_2=C(CH_3)CO_2CH_2C(CF_3)_2OH$ from Methacrylic Acid and HFIBO A 3-neck flask fitted with thermocouple, septum, and reflux condenser (5° C.) was charged with methacrylic acid (43.1 g, 0.5 mol) and benzyltriethyl ammonium chloride (1.14 g, 5.0 mmol). HFIBO (96.3 g, 0.535 mol) was added by means of a canula, starting at room temperature. The mixture was heated to reflux (ca. 48° C., liquid temperature). As the boil-up rate diminished, the bath temperature was increased so that reflux was re-established, but at higher residual liquid temperature. The reaction temperature was increased in stages to 85° C. and was maintained at this value for 0.5 hr.

$^1H$ NMR($C_6D_6$): 5.98 (m, approx. J=1.1 Hz, a=1.00), 5.15 (m, approx. J=1.5 Hz, 1.00), 4.35 (s, a=1.00, OH), 4.25 (s, a=2.00, $CH_2$), 1.64 (dd, J=1.1, 1.5 Hz, a=3.05), in accord with desired ester. No signals for methacrylic acid were observed.

$^{19}F$ NMR($C_6D_6$): −76.48 (s, a=95.4), −73.24 (s, a=4.6, starting epoxide).

Distillation (small spinning band) gave a forerun fraction, then the major fraction, 124 g, with b.p. 48.6° C./4.5 mm. $^1H$ NMR of the forerun showed only trace contaminant, so yield after distillation was ca. 94%, without consideration of column hold-up.

Example 6

Homopolymer of 2,2-bis(trifluoromethyl)-2-hydroxyethyl methacrylate

A solution of 2,2-bis(trifluoromethyl)-2-hydroxyethyl methacrylate (10.0 g) and 2,2'-azobisisobutryronitrile (250 mg) in ethyl acetate (15 mL) was added over a 20 min period to refluxing ethyl acetate (10 mL) in a 3-neck flask fitted with reflux condenser, thermocouple, and stir-bar. Reflux was continued for 3 hr after addition was complete. The resulting solution was cooled and added to hexane (300 mL) dropwise with rapid stirring. The supernatant was removed, and the precipitated polymer was treated with 150 mL hexane to produce tractable particles. The solid was filtered and air-dried to give 9.23 g of white solid after drying (vacuum oven, 50° C. ($N_2$ purge)

$^{19}F$ NMR (acetone-d6): −76.7 (brd m, width at half-height=30 Hz), minor signal intensity at −76.95.

$^1H$ NMR (acetone-d6): 4.50 to 4.25 (series of m, a=2.00), 2.82 (bd s, a=1.23), 1.95 (s, overlapping bd m), 1.55 to 0.9 (m).

$^1H$ NMR (THF-d8): 7.40 to 6.95 (signal envelope with multiple maxima, a=1.03, various OH), 4.44 to 4.14 (signal envelope with multiple maxima, major at 4.25, $CH_2$, total a=2.00), 2.2 to 0.8 (m, combined a=5.6, $CH_2$ and $CH_3$).

$^{19}F$ NMR (THF-d8); −76.95, −76.98 (overlapping).

SEC (THF, RI detector, polystyrene standards) showed: Mn=8960; Mw=15,900; Mw/Mn=1.77.

TGA ($N_2$): 2.1% weight loss 60-150° C.; onset of major loss at ca. 170° C.; 10% wt loss at 242° C.

DSC (second heat): weak transition at 68° C.

Example 7

A solution of the homopolymer (0.60 g in 3.4 g of 2-heptanone) prepared as described in Example 6 was used to spin-coat films on silicon wafers. It was found that film dissolution was too rapid for reliable dissolution rate measurement in 0.26 M tetramethylammonium hydroxide solution. A 40-fold dilution of base concentration allowed the observation of uniform dissolution of the film.

Example 8

Preparation of a Tetrapolymer Derived from $CH_2$=C($CH_3$)$CO_2CH_2C(CF_3)_2OH$ A 3-neck flask fitted with addition funnel and nitrogen gas inlet with adaptor to vacuum for de-gassing the reaction mixture, thermocouple, and stir-bar was charged with trithiocarbonate RAFT agent $C_{12}H_{25}SC(S)SC(CH_3)(CN)CH_2CH_2CO_2CH_3$ (9.13 g=22.0 mmol), methyl ethyl ketone (160 mL), 1-ethyl-cyclopentylmethacrylate (21.26 g), methyl adamantyl methacrylate (67.96 g), norbornene lactone methacrylate, $CH_2$=C($CH_3$)$CO_2CH_2C(CF_3)_2OH$ (35.05 g), V-601 (FW=230.26, 1.08 g, 4.7 mmol), and sodium bicarbonate $NaHCO_3$ (0.9 g). The reactor was filled with nitrogen, and two more evacuation/fill cycles were performed. The temperature was increased to 67° C. over 0.5 hr. After 22 hr, the reaction mixture was diluted with MEK (250 mL), cooled to room temperature, and filtered through glass fiber paper. The polymer solution was added to heptane (5600 mL) dropwise with rapid stirring. Polymer was collected by filtration, washed with heptane and air-dried overnight to give 199.5 g of light yellow solid (room temperature, $N_2$ stream). $^1H$ NMR showed no detectable acid groups or residual monomers: 7.20 (bd s, OH, a=1.00), 4.70 to 4.20 (overlapping signals), 3.20 (bd s with lower-field shoulder), 2.7 to 0.85 (series of bd m).

SEC analyses: Mw=8287; Mn=6998; PD=1.18

UV (THF, 1.000 g/liter, 1 cm): $A_{311.0}$=1.261.

The trithiocarbonate-derived end groups were removed from the polymer by treatment with $Et_3NH$ $H_2PO_2$ in the presence of radical initiator. The polymer (140 g) was charged to a 3 neck flask and dissolved in 2-butanone (175 mL). Triethylammonium hypophosphite ($Et_3NH$ $H_2PO_2$, 15.68 g) was added. V-501 (2.94 g) was added, and the reaction mixture was heated to 68° C.-70° C. and maintained for 3.5 hr. Another 0.6 g of V-501 was added, and reaction mixture was heated for another 1.5 hr.

The cooled polymer solution was filtered and added to cold methanol (2100 mL; 0° C.). The mixture was filtered, and the solid was washed with additional cold methanol (4×200 mL) and allowed to warm on the working filter under $N_2$ to provide 125.8 g white solid. The product was re-dissolved in MEK and precipitated in cold methanol as above to provide 120.8 g of white solid. $^1H$ NMR showed no detectable residual hypophosphite salt.

Example 9

Preparation of a Block Copolymer Containing $CH_2$=C($CH_3$)$CO_2CH_2C(CF_3)_2OH$ A 4-neck flask fitted with addition funnel and nitrogen gas inlet, thermocouple, and stir-bar is charged with trithiocarbonate RAFT agent $C_{12}H_{25}SC(S)SC(CH_3)(CN)CH_2CH_2CO_2CH_3$ (22.0 mmol), methyl ethyl ketone (150 mL), 1-ethyl-cyclopentylmethacrylate (21 g), methyl adamantyl methacrylate (68 g), norbornene lactone methacrylate (68 g), V-601 (4.7 mmol), and sodium bicarbonate $NaHCO_3$ (0.5 g). The reaction vessel is purged with nitrogen, and the temperature is increased to 70° C. over 0.5 hr. After 16 hr, when the above-named monomers are substantially consumed, solutions of $CH_2$=C($CH_3$)$CO_2CH_2C(CF_3)_2OH$ (35 g, in methyl ethyl ketone, 10 mL) and V-601 (2.5 mmol, in methyl ethyl ketone, 10 mL) are added simultaneously (2 hr) at 70° C. Reaction is maintained at 70° C. for 12 hr. Polymer solution is diluted with methyl ethyl ketone, filtered to remove $NaHCO_3$, and polymer is isolated by precipitation in heptane. Polymer composition is comparable to that obtained in Example 8, except that the fluoroalcohol monomers are not randomly distributed, but exist only in the second block.

Example 10

Preparation of a Block Copolymer Containing $CH_2$=C($CH_3$)$CO_2CH_2C(CF_3)_2OH$ A 4-neck flask fitted with addition funnel and nitrogen gas inlet, thermocouple, and stir-bar is charged with trithiocarbonate RAFT agent $C_{12}H_{25}SC(S)SC(CH_3)(CN)CH_2CH_2CO_2CH_3$ (10.0 mmol), methyl ethyl ketone (35 mL), V-601 (2 mmol), and $CH_2$=C($CH_3$)$CO_2CH_2C(CF_3)_2OH$ (35 g). The reaction vessel is purged with nitrogen, and the temperature is increased to 70° C. over 0.5 hr. After 16 hr, when the methacrylate monomer is substantially consumed, solutions of styrene (65 g) in methyl ethyl ketone, 60 mL) and t-butyl peroxy-2-ethylhexanoate (2.5 mmol, in methyl ethyl ketone, 10 mL) are added simultaneously (2 hr) at 75° C. After an 8 hr reaction period, the polymer is isolated by precipitation in hexane.

What is claimed is:

1. A process for the preparation of a fluoroalcohol-substituted (meth)acrylate ester of formula $CH_2=C(R)CO_2CH_2C(R_f)_2OH$, comprising reacting $CH_2=C(R)CO_2H$ with a fluorinated epoxide 3,

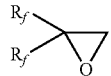

in the presence of a catalyst, wherein R is H or a $C_1$-$C_4$ alkyl group, and $R^f$ is a fluorinated $C_1$-$C_{10}$ alkyl group.

2. The process of claim 1, wherein $R^f$ is $CF_3$.

3. The process of claim 1, wherein R is H or $CH_3$.

4. The process of claim 1, wherein the catalyst is selected from the group consisting of PPN chloride and quaternary ammonium halides.

* * * * *